United States Patent [19]
Boaz

[11] Patent Number: 5,886,214
[45] Date of Patent: Mar. 23, 1999

[54] PROCESS FOR THE PRODUCTION OF CHIRAL UNSATURATED ALCOHOLS IN HIGH OPTICAL PURITY

[75] Inventor: Neil Warren Boaz, Kingsport, Tenn.

[73] Assignee: Eastman Chemical Company, Kingsport, Tenn.

[21] Appl. No.: 839,477

[22] Filed: Apr. 14, 1997

[51] Int. Cl.$^6$ ........................................... C07C 7/02
[52] U.S. Cl. ............................................ 560/261; 560/113
[58] Field of Search ...................... 560/261, 113

[56] References Cited

U.S. PATENT DOCUMENTS

| | | | |
|---|---|---|---|
| 5,360,938 | 11/1994 | Babin et al. | 568/449 |
| 5,491,266 | 2/1996 | Babin et al. | 568/449 |
| 5,736,480 | 4/1998 | Davis et al. | 502/155 |

OTHER PUBLICATIONS

Koenig, K. E.; Bachman, G. L.; Vineyard, B. D., *J. Org. Chem.* 1980, 45, 2362.

Selke, R.; Pracejus, H., *J. Mol. Cat.* 1986, 37, 213.

Brown, J. M.; Murrer, B. A., *J. Chem. Soc. Perkin Trans. 2* 1982, 489.

Fryzuk, M. D.; Bosnich, B., *J. Am. Chem. Soc.* 1978, 100, 5491.

Ohta, T.; Miyake, T.; Seido, N.; Kumobayashi, H.; Takaya, H. *J. Org. Chem.* 1995, 60, 357.

Burk, J., *J. Am. Chem. Soc.* 1991, 113, 8518.

Burgess, K.; Jennings, L. D., *J. Am. Chem. Soc.* 1991, 113, 6129.

Mori, K.; Ogita, H. *Leibigs Ann. Chem.* 1994, 1065.

Kim, H–S et al. J. Organomet. Chem. (1997) 545–546 337–344.

*Primary Examiner*—Paul J. Killos
*Attorney, Agent, or Firm*—Michael J. Blake; Karen A. Harding; Harry J. Gwinnell

[57] ABSTRACT

The catalytic asymmetric hydrogenation of enol esters with a vinyllic or acetylenic substituent proceeds with extremely high enantioselectivity using a Rhodium-chiral bisphosphine catalyst. This is at variance with the hydrogenation of enol esters bearing a saturated substituent, which are hydrogenated with only marginal enantioselectivity under the same conditions.

20 Claims, No Drawings

PROCESS FOR THE PRODUCTION OF CHIRAL UNSATURATED ALCOHOLS IN HIGH OPTICAL PURITY

BACKGROUND OF THE INVENTION

Chiral alcohols are among the most versatile of chiral materials due to the ready transformation of the hydroxyl substituent into a myriad of other functional groups. These materials find numerous industrial uses due to their ready incorporation into chiral pharmaceutical and agrochemical agents.

Allylic alcohols are an especially important subset of chiral alcohols, since the olefin allows remote functionalization and transformation into various other groups while retaining the chiral information inherent in the alcohol educt. Efficient and inexpensive methods to prepare these types of chiral species in high optical purity are lacking, especially since pharmaceutical/agrochemical use require optical purities of at least 95% enantiomeric excess, (% enantiomer A-% enantiomer B or ee). Catalytic asymmetric reactions are among the most efficient methods available to generate asymmetry. Unfortunately, most asymmetric synthetic methods for the preparation of chiral alcohols are best suited for the preparation of compounds with an aromatic substituent immediately adjacent to the chiral center, and the technologies usually afford products of low enantiomeric excess without this type of structural feature. Indeed, there are no general methods to prepare chiral allylic alcohols or derivatives in high optical purity and in high yield through catalytic means. One approach would be through hydrogenation of enol esters.

PRIOR ART

The following references describe the catalytic asymmetric hydrogenation of enol esters with various catalysts: Koenig, K. E.; Bachman, G. L.; Vineyard, B. D. *J. Org. Chem.* 1980, 45, 2362. Selke, R.; Pracejus, H. *J. Mol. Cat.* 1986, 37, 213. Brown, J. M.; Murrer, B. A. *J. Chem. Soc. Perkin Trans.* 2 1982, 489. Fryzuk, M. D.; Bosnich, B. *J. Am. Chem. Soc.* 1978, 100, 5491. However, the foregoing processes yielded only moderate enantioselectivities.

The reduction of cyclic enol esters with moderate to high enantioselectivity using a ruthenium catalyst with an optically pure 2,2'-bis(diphenylphosphino)-1,1'-binaphthyl (BINAP) ligand has been disclosed by Ohta,T.; Miyake, T.; Seido, N.; Kumobayashi, H.; Takaya, H. *J. Org. Chem.* 1995, 60, 357. None of the substrates investigated were aliphatic enol esters, and the hydrogenation of acetophenone enol acetate using this system afforded only poor to moderate enantioselectivity.

High enantioselectivity has been observed for the asymmetric hydrogenation of enol esters using a rhodium(I) catalyst prepared using the chiral ligand 1,2-Bis(2,5-dialkylphospholano)benzene (DuPHOS) as reported by Burk, M. J. *J. Am. Chem. Soc.* 1991, 113, 8518. The substrates reported had substituents that varied from aromatic to carboethoxy to trifluoromethyl, and were uniformly hydrogenated with ≧89% ee. None of the substrates investigated were aliphatic or olefinic enol esters. There are no examples of catalytic hydrogenation methods to afford aliphatic or allylic alcohols or derivatives.

DESCRIPTION OF THE INVENTION

The present invention discloses a process comprising the step of converting dienol or enynol esters to chiral allylic alcohol esters via asymmetric hydrogenation in the presence of a rhodium catalyst and a chiral bisphosphine ligand. Generally, the allylic alcohol ester has an enantiomeric purity of at least about 90% ee. Examples of the process of the present invention are shown below.

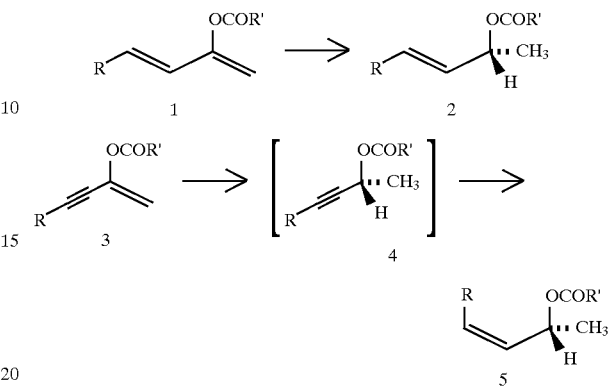

Thus, this invention pertains to a novel process for the asymmetric hydrogenation of enol esters to afford chiral alcohol esters in high optical purity. More specifically, this invention pertains to the catalytic asymmetric hydrogenation of enol esters bearing a vinyllic or an acetylenic substituent (structural types 1 and 3, respectively) through the use of a chiral rhodium(I) catalyst prepared from a suitable rhodium salt and an optically pure commercially available ligand.

It has been unexpectedly found that chiral allylic alcohol esters may be made in optical purities of at least about 90% ee via the asymmetric hydrogenation of dienol esters (structural type 1) or enynol esters (structural type 3) using a rhodium catalyst with a chiral bisphosphine ligand. This is particularly surprising as asymmetric hydrogenation of the aliphatic enol ester counterparts to 1 or 3 yield products having much lower (<80% ee) optical purity.

The dienol esters of Formula 1 may be any compound of Formula 1 wherein R and R' are the same or different and are, for example, alkyl (1–20 carbons), substituted $C_{1-20}$ alkyl (wherein the substituents include alkoxy, ester, halide, ketone, and olefin), $C_{6-20}$ aryl, $C_{6-20}$ substituted aryl (wherein the substituents include alkoxy, ester, halide, ketone, and olefin), or $C_{4-20}$ heteroaryl (wherein the hetero groups are selected from S, N, O). Suitable dienol esters may be readily prepared from the corresponding enone. For example, suitable dienyl acetates can be prepared by reaction with isopropenyl acetate under acid catalysis. These reactions are most often performed at reflux with isopropenyl acetate as the solvent utilizing a mineral or sulfonic acid catalyst.

The enynol esters of Formula 3 may be any compound of Formula 3 wherein R are R' are the same or different and are, for example, alkyl (1–20 carbons), substituted $C_{1-20}$ alkyl (wherein the substituents include alkoxy, ester, halide, ketone, and olefin), $C_{6-20}$ aryl, $C_{6-20}$ substituted aryl (wherein the substituents include alkoxy, ester, halide, ketone, and olefin), or $C_{4-20}$ heteroaryl (wherein the hetero groups are selected from N, O, S). Suitable enynol esters may be prepared from the corresponding α,β-acetylenic ketones by enolate formation using a strong base such as a dialkylamide at low temperature (−78° C.) in an ethereal solvent such as THF. The enolate formation is followed by reaction with an acid anhydride and warming to ambient temperature.

The dienol or enynol ester is converted into the desired allylic alcohol ester in the presence of a chiral rhodium catalyst under hydrogenation conditions.

The catalysts used for these transformations are rhodium (I) species (such as A) prepared either discretely or in situ from a suitable rhodium salt such as bis(1,5-cyclooctadienyl)rhodium (I) tetrafluoroborate (which is able from Aldrich Chemical Company) and a chiral bisphosphine ligand.

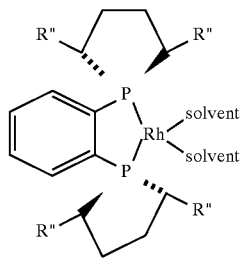

A

Generally up to about 2 mol % of catalyst may be used. The amount of catalyst used is usually between about 0.05 and 2 mol percent. It should be understood that the reaction rate increases with increasing amount of catalyst and thus, between about 0.5 and 2 mol percent of catalyst is preferred for a very rapid reduction. Generally, between about 0.5 mol percent and about 1 mol percent catalyst is sufficient to provide a reasonable reaction rate.

The preferable ligands for this transformation include the various chiral DuPHOS ligands 6, most preferably the optically pure DuPHOS species wherein R" is selected from alkyl groups having 1 to 4 carbon atoms, of the formula

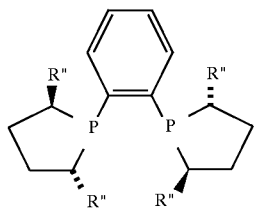

6

Several of these compounds with different R" groups are commercially available from Strem Chemical.

The hydrogenation reactions are normally conducted at a temperature between the freezing and boiling point (or apparent boiling point if under pressure) of the solvent and a pressure of between about 1 atm and about 100 atm. Preferably, the reactions are run between about −20° C. and about 100° C., and most preferably between about 0° C. and 65° C. It should be noted that higher temperatures and pressures generally afford more rapid reactions. The examples reported below were run at ambient temperature, since this allows sufficient reactivity while not sacrificing enantioselectivity.

The acceptable solvents for the hydrogenations include $C_{5-10}$ hydrocarbons, $C_{1-10}$ cyclic and alicyclic ethers, $C_{3-10}$ esters, $C_{3-10}$ ketones, and lower alcohols having 1 to 5 carbon atoms. More preferable are $C_{1-10}$ cyclic and alicyclic ethers and lower alcohols having 1 to 5 carbon atoms. The most preferable solvents are tetrahydrofuran and methanol. The concentration of the dienol or enynol esters can vary between about 0.1 and about 2M in these solvents.

The optical purities of the products were determined by chiral capillary GC using a chiral Cyclodex-B column (J&W Scientific). For comparison purposes, a control chromatogram of an independently prepared racemic mixture served to verify the identity and resolution of the enantiomeric peaks. The absolute configuration of the products of these reductions was ultimately determined by a comparison of the optical rotation of the product with a literature value.

Within the same family, chemical interconversion along with elution order on chiral GC allowed absolute configurational assignment for each reduction.

EXAMPLES

Example 1

Catalytic Asymmetric Hydrogenation of 1,3-Nonadien-2-yl Acetate

Bis(cyclooctadienyl)rhodium tetrafluoroborate (10 mg; 0.005 mmol; 0.02 equiv) and R,R-1,2-bis(2,5-dimethylphospholano)benzene (6, R"=CH$_3$; 9 mg; 0.03 mmol; 0.006 equiv) were combined in a pressure tube equipped with a magnetic stir bar under argon. The tube was evacuated and filled with argon five times, and then 2.5 mL of degassed tetrahydrofuran (THF) was added to afford a yellow-orange solution. 1,3-Nonadien-2-yl acetate (1a; 911 mg; 5 mmol) dissolved in 2.5 mL of degassed THF was then added. The reaction mixture was evacuated and filled with argon five times and then was evacuated and filled with hydrogen three times. The reaction mixture was placed under 30 psi of hydrogen and stirred at room temperature overnight, at which time hydrogen uptake had ceased. The vessel was vented and flushed with nitrogen, and the reaction mixture was concentrated to afford 981 mg of crude 3-nonen-2-yl acetate (2a) containing a small amount of the fully saturated analog. Analysis of this material by chiral GC and comparing to authentic racemate showed a 96:4 ratio of enantiomers (92% ee). Conversion to 2-nonanol (hydrolysis and hydrogenation) and comparison with authentic material indicated the (R) absolute configuration. Thus, the asymmetric hydrogenation of the present invention yielded the desired product having high optical purity. The spectra is shown below:

$^1$H NMR (CDCl$_3$) δ 5.694 (1H, dtd, J=0.86, 6.68, 15.29 Hz); 5.446 (1H, tdd, J=1.43, 6.81, 15.33 Hz); 5.305 (1H, m(5), J=6.47 Hz); 2.034 (3H, s); 2.0 (2H, m); 1.4–1.2 (6H, m); 1.286 (3H, d, J=6.44 Hz); 0.880 (3H, t, J=7.05 Hz). Chiral GC (30 m Cyclodex-B column [J&W Scientific], 90° C.): $t_R$(S) 15.260 min; $t_R$(R) 16.663 min.

Example 2

Catalytic Asymmetric Hydrogenation of 4-phenyl-1,3-butadien-2-yl Acetate

This reaction was performed as in Example 1 with bis(cyclooctadienyl)rhodium tetrafluoroborate (20 mg; 0.05 mmol; 0.02 equiv), R,R-1,2-bis(2,5-dimethylphospholano)benzene (6, R"=CH$_3$; 18 mg; 0.06 mmol; 0.024 equiv) and 4-phenyl-1,3-butadien-2-yl acetate (1b; 471 mg; 2.5 mmol) in 20 mL of degassed THF. The crude product (0.46 g) was flash-chromatographed and eluted with 1:4 ethyl acetate: heptane to afford 352 mg (74%) of R-4-phenyl-3-buten-2-yl acetate (2b). Chiral GC analysis and comparison with authentic racemate indicated 93.6% ee for R-4-phenyl-3-buten-2-yl acetate. The (R) configuration was indicated by the optical rotation, $[\alpha]_D^{25}$+83.7° C. (c 2.03, CHCl$_3$), as compared with the literature value for the (R) enantiomer ($[\alpha]_D$+93.2° C. (c 2.37, CHCl$_3$) (Burgess, K.; Jennings, L. D. J. Am. Chem. Soc. 1991, 113, 6129).

$^1$H NMR (CDCl$_3$) δ 7.4–7.2 (5H, m); 6.612 (1H, d, J=15.87 Hz); 6.199 (1H, dd, J=6.75, 15.99 Hz); 5.536 (1H, m(5), J=6.53 Hz); 2.085 (3H, s); 1.421 (3H, d, J=6.50 Hz). Chiral GC (30 m Cyclodex-B column [J&W Scientific], 125° CC): $t_R$(S) 17.847 min; $t_R$(R) 18.553 min.

Example 3

Catalytic Asymmetric Hydrogenation of non-1-en-3-yn-2-yl Acetate

This reaction was performed as in Example 1 with bis(cyclooctadienyl)rhodium tetrafluoroborate (10 mg; 0.025 mmol; 0.02 equiv), R,R-1,2-bis(2,5-dimethylphospholano)benzene (6, R"=CH$_3$; 9 mg; 0.03 mmol; 0.024 equiv) and non-1-en-3-yn-2-yl acetate (3a; 225 mg; 1.25 mmol) in 10 mL of degassed THF until hydrogen uptake ceased to afford 0.26 g of crude product. $^1$H NMR analysis indicated Z-non-3-en-2-yl acetate (5a) as the sole product, and reduction of the olefin followed by chiral GC analysis and comparison to racemate indicated 98.5% ee. The absolute configuration was determined to be (R) by reduction of the olefin of Z-non-3-en-2-yl acetate to 2-nonyl acetate, and comparison with authentic material.
$^1$H NMR (CDCl$_3$) δ 5.642 (1H, m); 5.498 (1H, td, J=6.90, 11.35 Hz); 5.364 (tdd, J=1.41, 8.85, 10.68 Hz); 2.2–2.0 (2H, m); 2.027 (3H, s); 1.4–1.2 (6H, m); 1.276 (3H, d, J=6.22 Hz); 0.885 (3H, t, J=6.84 Hz). Chiral GC of 2-nonyl acetate (30 m Cyclodex-B column [J&W Scientific], 100° C.): t$_R$(S) 9.634 min; t$_R$(R) 10.395 min.

Example 4

Catalytic Asymmetric Hydrogenation of 4-phenylbut-1-en-3-yn-2-yl Acetate

This reaction was performed as in Example 1 with bis(cyclooctadienyl)rhodium tetrafluoroborate (10 mg; 0.025 mmol; 0.02 equiv), R,R-1,2-bis(2,5-dimethylphospholano)benzene (6, R"=CH$_3$; 9 mg; 0.03 mmol; 0.024 equiv) and 4-phenylbut-1-en-3-yn-2-yl acetate (3b; 233 mg; 1.25 mmol) in 10 mL of degassed THF until hydrogen uptake ceased to afford 0.25 g of crude product. $^1$H NMR analysis indicated Z-4-phenyl-3-buten-2-yl acetate (5b) as the sole product, and reduction of the olefin to afford 4-phenyl-2-butyl acetate followed by chiral GC analysis and comparison to the racemate and authentic R-4-phenyl-2-butyl acetate indicated 97.8% ee for R-Z-4-phenyl-3-buten-2-yl acetate. Further investigation indicated a bimodal reduction, with 4-phenylbut-1-en-3-yn-2-yl acetate initially chemoselectively and enantioselectively reduced to 4-phenylbut-3-yn-2-yl acetate (4b), which was then more slowly reduced to Z-4-phenyl-3-buten-2-yl acetate (5b).
$^1$H NMR (CDCl$_3$) δ 7.4–7.2 (5H, m); 6.540 (1H, d, J=11.66 Hz); 5.817 (1H, qd, J=5.68, 8.25 Hz); 5.665 (1H, dd, J=9.16, 11.66 Hz); 2.028 (3H, s); 1.385 (3H, d, J=6.17 Hz). Chiral GC of 4-phenyl-2-butyl-acetate (30 m Cyclodex-B column [J&W Scientific], 125° C.): t$_R$(S) 11.683 min; t$_R$(R) 12.126 min.

Example 5

Catalytic Asymmetric Hydrogenation of 6-benzyloxyhex-1-en-3-yn-2-yl Acetate

This reaction was performed as in Example 1 with bis(cyclooctadienyl)rhodium tetrafluoroborate (10 mg; 0.025 mmol; 0.02 equiv), R,R-1,2-bis(2,5-dimethylphospholano)benzene (6, R"=CH$_3$; 9 mg; 0.03 mmol; 0.024 equiv) and 6-benzyloxyhex-1-en-3-yn-2-yl acetate (3c; 305 mg; 1.25 mmol) in 10 mL of degassed THF until hydrogen uptake ceased to afford 318 mg of crude product. $^1$H NMR analysis indicated Z-6-benzyloxyhex-3-en-2-yl acetate (5c) as the sole product, and reduction of the olefin to 6-benzyloxy-2-hexyl acetate followed by chiral GC analysis and comparison to racemate indicated >98% ee for R-Z-6-benzyloxyhex-3-en-2yl acetate.
$^1$H NMR (CDCl$_3$) d 7.35 (5H, m); 5.65 (1H, m); 5.578 (1H, td, J=7.14, 10.99 Hz); 5.462 (1H, dd, J=8.85, 10.75 Hz); 4.519 (2H, s); 3.516 (2H, m); 2.477 (2H, q, J=6.90 Hz); 2.017 (3H, s); 1.277 (3H, d, J=6.60 Hz). Chiral GC of 6-benzyloxy-2-hexyl acetate (30 m Cyclodex-B column [J&W Scientific], 165° C.): t$_R$(S) 14.229 min; t$_R$(R) 15.149 min.

Comparative Example 1

Catalytic Asymmetric Hydrogenation of non-1-en-2-yl Acetate

This reaction was performed as in Example 1 with bis(cyclooctadienyl)rhodium tetrafluoroborate (10 mg; 0.025 mmol; 0.01 equiv), R,R-1,2-bis(2,5-dimethylphospholano)benzene (6, R"=CH$_3$; 9 mg; 0.03 mmol; 0.012 equiv) and non-1-en-2-yl acetate (461 mg; 2.5 mmol) in 10 mL of degassed THF until hydrogen uptake ceased (2 h) to afford 0.46 g of crude product. $^1$H NMR analysis indicated 2-nonyl acetate as the sole product, and chiral GC analysis and comparison to racemate indicated 64.0% ee for 2-nonyl acetate. Hydrolysis of the acetate to 2-nonanol and comparison of the optical rotation, [α]$_D^{24}$–13.9° (c 1.15, benzene), with the literature value for the (S) enantiomer, [α]$_D^{18}$+11.4° (c 1.30, benzene) (Mori, K.; Ogita, H. Leibigs Ann. Chem. 1994, 1065.), indicated the (R) configuration for 2-nonyl acetate.
$^1$H NMR (CDCl$_3$) δ 4.886 (1H, m(6), J=6.93 Hz); 2.029 (3H, s); 1.6–1.2 (12H, m); 1.202 (3H, d, J=6.26 Hz); 0.879 (3H, t, J=6.53 Hz). Chiral GC (30 m Cyclodex-B column [J&W Scientific], 100° C.): t$_R$(S) 9.634 min; t$_R$(R) 10.395 min.

Comparative Example 2

Catalytic Asymmetric Hydrogenation of 4-phenylbut-1-en-2-yl Acetate

This reaction was performed as in Example 1 with bis(cyclooctadienyl)rhodium tetrafluoroborate (20 mg; 0.05 mmol; 0.02 equiv), R,R-1,2-bis(2,5-dimethylphospholano)benzene (6, R"=CH$_3$; 18 mg; 0.06 mmol; 0.024 equiv) and 4-phenylbut-1-en-2-yl acetate (476 mg; 2.5 mmol) in 20 mL of degassed THF until hydrogen uptake ceased (1.5 h) to afford 0.51 g of crude product. $^1$H NMR analysis indicated 4-phenyl-2-butyl acetate as the sole product, and chiral GC analysis and comparison to racemate indicated 77% ee for 4-phenyl-2-butyl acetate. Base hydrolysis afforded 4-phenyl-2-butanol, [α]$_D^{25}$–12.0° (c 2.115, CHCl$_3$), which indicates the (R) configuration when compared with the known rotation ([α]$_D$+13.5° (c 2.1, CHCl$_3$)) for the (S) enantiomer.
1H NMR (CDCl$_3$) δ 7.35–7.15 (5H, m); 4.946 (1H, m(6), J=6.53 Hz); 2.65 (2H, m); 2.039 (3H, s); 1.95 (1H, m); 1.8 (1H, m); 1.259 (3H, d, J=6.11 Hz). Chiral GC (30 m Cyclodex-B column [J&W Scientific], 125° C.): t$_R$(S) 11.683 min; t$_R$(R) 12.126 min.

Comparative Example 3

Catalytic Asymmetric Hydrogenation of 5-acetoxy-5-hexenyl Tosylate

This reaction was performed as in Example 1 with bis(cyclooctadienyl)rhodium tetrafluoroborate (10 mg; 0.025 mmol; 0.02 equiv), R,R-1,2-bis(2,5-dimethylphospholano)benzene (6, R"=CH$_3$; 9 mg; 0.03 mmol; 0.024 equiv) and 5-acetoxy-5-hexenyl tosylate (389 mg; 1.25 mmol) in 10 mL of degassed THF until hydrogen uptake ceased (1 h) to afford 407 mg of crude product.
$^1$H NMR analysis indicated 5-acetoxyhexyl tosylate as the sole product, and hydrolysis of the acetate, conversion of the resulting 5-hydroxyhexyl tosylate to the α-methoxy-α-trifluoromethylphenylacetate (using the corresponding optically pure acid chloride), $^1$H NMR analysis and comparison to the racemate indicated 78% ee for 5-acetoxyhexyl tosylate.

$^1$H NMR (CDCl$_3$) δ 7.792 (2H, d, J=8.36 Hz); 7.353 (2H, d, J=8.03 Hz); 4.830 (1H, m(6), J=5.22 Hz); 4.020 (2H, t, J=6.38 Hz); 2.456 (3H, s); 2.017 (3H, s); 1.7–1.2 (6H, m); 1.174 (3H, d, J=6.32 Hz).

Comparative Example 4

Catalytic Asymmetric Hydrogenation of Ethyl 5-acetoxyhex-5-enoate

This reaction was performed as in Example 1 with bis(cyclooctadienyl)rhodium tetrafluoroborate (10 mg; 0.025 mmol; 0.02 equiv), R,R-1,2-bis(2,5-dimethylphospholano)benzene (6, R"=CH$_3$; 9 mg; 0.03 mmol; 0.024 equiv) and ethyl 5-acetoxyhex-5-enoate (ca. 50% pure; 500 mg; 1.25 mmol) in 10 mL of degassed THF until hydrogen uptake ceased (1 h) to afford 490 mg of crude product. $^1$H NMR analysis indicated ethyl 5-acetoxyhexanoate as the sole product, and chiral GC analysis (30 m Cyclodex-B column (J&W Scientific), 120° C., 20 min) and comparison to racemate indicated 72% ee for ethyl 5-acetoxyhex-5-enoate. $^1$H NMR (CDCl$_3$) δ 4.894 (1H, m(6), J=6.25 Hz); 4.123 (2H, q, J=6.17 Hz); 2.3 (2H, m); 2.025 (3H, s); 1.7– 1.5 (4H, m); 1.250 (3H, t, J=7.14 Hz); 1.214 (3H, d, J=6.93 Hz). Chiral GC (30 m Cyclodex-B column [J&W Scientific], 120° C.): t$_R$(S) 12.16 min; t$_R$(R) 12.75 min.

Comparative Example 5

Catalytic Asymmetric Hydrogenation of Ethyl 5-acetoxyhex-5-enoate Using BINAP Ligand This reaction was performed as in Example 1 with bis(cyclooctadienyl)rhodium tetrafluoroborate (10 mg; 0.025 mmol; 0.02 equiv), R,R-2,2'-bis(diphenylphosphino)-1,1'-binaphthyl (R,R-BINAP) (18 mg; 0.03 mmol; 0.024 equiv), and ethyl 5-acetoxyhex-5-enoate (ca. 50% pure; 500 mg; 1.25 mmol) in 10 mL of degassed THF overnight to afford 490 mg of crude product. $^1$H NMR analysis indicated ethyl 5-acetoxyhexanoate as the sole product (although much residual ethyl 5-acetoxyhex-5-enoate was noted), and chiral GC analysis (30 m Cyclodex-B column (J&W Scientific), 120° C., 20 min) and comparison to racemate indicated 32% ee for ethyl 5-acetoxyhexanoate.

Table 1, below summarizes the results of Examples 1–5 and Comparative Examples 1–5.

TABLE 1

| Ex. # | Product | optical purity (% ee) |
|---|---|---|
| 1 | 3-nonen-2-yl acetate | 92 |
| 2 | 4-phenyl-3-buten-2-yl acetate | 93.6 |
| 3 | Z-non-3-en-2-yl acetate | 98.5 |
| 4 | Z-4-phenyl-3-buten-2-yl acetate | 97.8 |
| 5 | Z-6-benzyloxyhex-3-en-2-yl acetate | >98 |
| CE 1 | 3-nonyl acetate | 64 |
| CE 2 | 4-phenyl-2-butyl acetate | 77 |
| CE 3 | 5-acetoxyhexyl tosylate | 78 |
| CE 4 | ethyl 5-acetoxyhexanoate | 72 |
| CE 5 | ethyl 5-acetoxyhexanoate | 32 |

Clearly the optical purities afforded by the hydrogenation of a aliphatic enol ester compound (Comparative Examples 1–5) are not suitable for pharmaceutical and agricultural uses.

There was no reason to expect that including unsaturation would lead to improved results. Thus, it was very surprising to find that the enantioselectivity of the catalytic asymmetric hydrogenation of the substrates used in Examples 1 and 2 (structural type 1) was greatly enhanced compared to the aliphatic species (Comparative Examples 1 and 2). For example, the catalytic asymmetric hydrogenation of 1,3-nonadien-2-yl acetate (Example 1) afforded an optical purity of 94% ee, whereas the aliphatic analog non-1-en-2-yl acetate afforded only 64% ee using the same catalyst and conditions. As is shown by Example 2 this high enantioselectivity was not limited to one particular substrate.

Even more surprising were the results obtained for the asymmetric hydrogenation of acetylenic substrates of structural type 3 (Examples 3–5). These types of compounds afforded under the standard asymmetric hydrogenation conditions a bimodal reduction, initially affording propargyllic alcohol ester 4. This material underwent further reduction to afford the Z-allylic acetate 5. The enantioselectivity engendered in the initial reduction step is greater than about 97% ee, which was surprising in view of the selectivities of the aliphatic enol esters. Moreover, this type of enantioselectivity is in the range that is considered useful for pharmaceutical and agrochemical use. Examples 3–5 clearly indicate that this type of enantioselectivity is general for structures of type 3.

We claim:

1. A process comprising the step of converting a dienol or enynol ester to a chiral allylic alcohol ester via asymmetric hydrogenation in the presence of a rhodium catalyst, at least one solvent and a chiral bisphosphine ligand.

2. The process of claim 1 wherein said allylic alcohol ester has an enantiomeric purity of at least about 90% ee.

3. The process of claim 1 wherein said dienol ester is compound of formula 1:

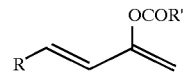

wherein R and R' may be the same or different and are selected from the group consisting of C$_{1-20}$ alkyl, substituted C$_{1-20}$ alkyl, C$_{6-20}$ aryl, substituted C$_{6-20}$ aryl and C$_{4-20}$ heteroaryl.

4. The process of claim 1 wherein said enynol ester is compound of formula 3:

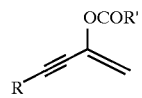

wherein R and R' may be the same or different and are selected from the group consisting of C$_{1-20}$ alkyl, substituted C$_{1-20}$ alkyl, C$_{6-20}$ aryl, substituted C$_{6-20}$ aryl and C$_{4-20}$ heteroaryl.

5. The process of claim 1 wherein said rhodium catalyst is a rhodium(I) species of the formula:

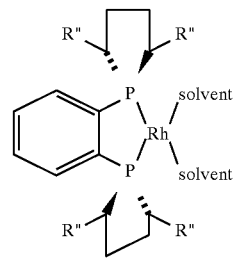

wherein each R" may be the same or different and is selected from the group consisting of alkyl groups having 1 to 4 carbon atoms.

6. The process of claim 5 wherein said rhodium catalyst is prepared from a rhodium salt and a chiral ligand.

7. The process of claim 5 wherein up to about 2 mol percent of said catalyst is used.

8. The process of claim 5 wherein between about 0.5 and about 2 mol percent of catalyst is used.

9. The process of claim 5 wherein between about 0.5 mol % and about 1 mol percent catalyst is used.

10. The process of claim 5 wherein said chiral ligand is a compound of the formula

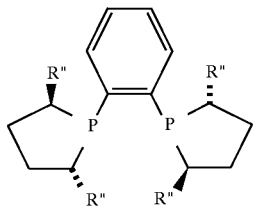

wherein R" may be the same or different and is selected from the group consisting of alkyl groups having 1 to 4 carbon atoms.

11. The process of claim 1 wherein said converting step is conducted at a temperature between the freezing and boiling point or, if under pressure, the apparent boiling point of the solvent.

12. The process of claim 1 wherein said converting step is conducted at a temperature between about −20° C. and about 100° C.

13. The process of claim 1 wherein said converting step is conducted at a temperature between about 0° C. and 65° C.

14. The process of claim 1 wherein said converting step is conducted at a pressure between about 1 atm and about 100 atm.

15. The process of claim 1 wherein said converting step is conducted at a pressure between about 1 and about 5 atm.

16. The process of claim 1 wherein said solvent is selected from the group consisting of $C_{5-10}$ hydrocarbons, $C_{2-10}$ cyclic or alicyclic ethers, $C_{3-10}$ esters, $C_{3-10}$ ketones, and $C_{1-5}$ lower alcohols and mixtures thereof.

17. The process of claim 1 wherein said solvent is selected from the group consisting of $C_{2-10}$ cyclic or alicyclic ethers and $C_{1-5}$ lower alcohols.

18. The process of claim 1 wherein said solvent is tetrahydrofuran or methanol.

19. The process of claim 1 wherein said dienol or enynol esters is present in said solvent in a concentration between about 0.1 and about 2M.

20. A process comprising the step of converting an enynol ester to a propargyllic alcohol ester via asymmetric hydrogenation in the presence of a rhodium catalyst, at least one solvent and a chiral bisphophine ligand.

* * * * *